United States Patent
Currier

(10) Patent No.: US 7,033,400 B2
(45) Date of Patent: Apr. 25, 2006

(54) PROSTHETIC COUPLING DEVICE

(76) Inventor: Mark R. Currier, 292 St. James Ave., Milton, NH (US) 03851

( * ) Notice: Subject to any disclaimer, the term of this patent is extended or adjusted under 35 U.S.C. 154(b) by 0 days.

(21) Appl. No.: 10/216,105

(22) Filed: Aug. 8, 2002

(65) Prior Publication Data

US 2004/0028467 A1 Feb. 12, 2004

(51) Int. Cl.
*A61F 2/80* (2006.01)

(52) U.S. Cl. ............................................ 623/33; 425/2

(58) Field of Classification Search ................. 623/33, 623/36, 34, 901; 264/222, DIG. 30; 425/2; 249/55
See application file for complete search history.

(56) References Cited

U.S. PATENT DOCUMENTS 5,728,166 A * 3/1998 Slemker ...................... 623/36
6,273,918 B1 * 8/2001 Yuhasz et al. ................ 623/33

FOREIGN PATENT DOCUMENTS

| DE | 43 21 182 C1 | * 12/1994 | |
|---|---|---|---|
| GB | 778563 | * 7/1957 | .................. 623/33 |
| RU | 2 142 758 C1 | * 12/1999 | |

* cited by examiner

Primary Examiner—David H. Willse
(74) Attorney, Agent, or Firm—Dauphin Law Offices

(57) ABSTRACT

A prosthetic coupling device for incorporation into a prosthetic socket and for coupling a prosthetic limb structural system to the prosthetic socket includes a deformable urethane cup to receive a positive model of an amputated limb and a coupling plate for attaching the prosthetic socket to prosthetic limb structural system. The deformable cup is flared at an end to allow it to accommodate a wide range of limb sizes. The coupling plate includes a surface for attaching to the deformable urethane cup, threaded standoffs that adjust the thickness of a laminate material formed around the end of the coupling plate during fabrication into a prosthetic socket, an o-ring that secures a sheet of PVA to the coupling plate during fabrication and a centered through hole for connecting to a pin from a suspension sleeve. The prosthetic coupling device may further include one or more magnets for releasably securing the prosthetic socket to a suspension sleeve.

14 Claims, 10 Drawing Sheets

PROSTHETIC COUPLING DEVICE

FIELD OF THE INVENTION

The present invention is directed generally to prosthetic limb systems and more specifically to a prosthetic coupling device for use with lower extremity prosthetic limb systems.

BACKGROUND OF THE INVENTION

Lower extremity endoskeletal and exoskeletal prostheses, those prosthetic limb systems that are used to replace an amputated portion of a leg and to help restore the amputee's ability to use that leg, are commonly grouped into two categories; above-knee and below knee devices. Both of these types of lower extremity prosthetic limb systems are made to attach to the distal end of an amputated limb and will often include a roll-on suspension sleeve, which attaches directly to the limb, a prosthetic limb socket, which is mechanically or magnetically attached to the suspension sleeve and a prosthetic structural system, which is mechanically attached to a prosthetic coupling mechanism formed within the prosthetic limb socket.

An important consideration in the design of lower extremity prosthetic systems is the strength of the prosthetic socket design and coupling system since the socket is the load-bearing interface between the residual limb and the load bearing prosthetic structural system. Other important considerations are the simplicity of the design and the method of fabrication of the prosthetic socket, as each prosthetic socket must be custom fit to an individual.

Fabrication of lower extremity prostheses typically begins with the making of a positive model of the residual limb or stump. This may be accomplished by a variety of methods, the most common encompasses wrapping the limb with plaster-of-Paris bandages, allowing the bandages to dry thereby creating a negative mold and then filling the negative mold with a mixture of plaster-of-Paris and water and allowing it to harden. Other, more advanced methods for creating positive residual limb models include the use of computer-aided-design (CAD) and computer-aided-manufacturing (CAM) systems with three-dimensional printers. The positive model may then be modified in a number of ways by a skilled prosthetist to accommodate for various weight-bearing and non-weight-bearing surfaces.

Using the modified positive model an intimate fitting prosthetic socket may be formed by means of thermo-molding or thermosetting techniques. During fabrication of the prosthetic socket, an attachment plate or similar coupling device is usually formed within an end of the prosthetic socket, which allows a prosthetic structural system to be bolted or otherwise connected to the prosthetic socket. A variety of prior art attachment plates (e.g. Grace Plate) are available, the most common of which include a standard four hole pattern (e.g., the Otto-Bock European pattern or the USMC pattern).

Another important goal when making a prosthetic socket is that the coupling device most be properly positioned with respect to the positive model in order to fit and function properly. With prior art prosthetic systems this goal is often difficult to achieve. For example, one common prior art coupling system employs a three-prong adapter mechanism for positioning the coupling device on the positive model. This system requires that the three prongs be bent and shaped to the contours of a positive model. Because the three prongs do not create an intimate contact with the positive model a resin material is added to the coupling device to make up this space. After the resin hardens the three-prong adapter may not be repositioned, if it is later determined that the coupling device is not properly aligned with the positive model. Still other systems require that the positive model be reshaped so that an attachment plate will be at a correct degree.

As a convenience in locating the attachment plate holes after the prosthetic socket is formed, cap head screws are typically placed in the holes. After fabrication of the socket, the thermo-molded or thermoset material will be higher over the screw heads than in surrounding areas and may be ground away to expose the screw heads. The screws may then be removed with an Allen Wrench exposing the plate holes. Even with the use of the cap head screws, finishing the end of the socket can be very time consuming.

Other systems, such as the Becker Orthopedic Model 403000 Plate, which incorporates a knurled surface, eliminate the need to vacuum form plastic on the underside of the attachment plate. Although these attachment plates reduce the time and effort required to finish the plate they employ a fingertip type grip between the plate and the laminated material, which is a substantially weaker bond than the above-described fabrication methods.

These and other prior art systems are effective in attaching a lower extremity prosthetic limb system to an amputated limb, however, because each prosthetic socket must be custom designed to an individual, these systems can be difficult and time-consuming to manufacture. Therefore, it is desirable to have a prosthetic limb system that is more quickly and easily fabricated without sacrificing the structural integrity of the prosthetic socket. It is also desirable to have a prosthetic limb system that has enhanced structural features and that is easier to attach to an amputated limb.

SUMMARY OF THE INVENTION

Embodiments of the present invention provide an apparatus and method for coupling a prosthesis limb structural assembly to a prosthetic limb socket.

In accordance with one embodiment of the present invention, a coupling system includes a deformable cup and a coupling plate operatively connected to the deformable cup.

In another embodiment the deformable cup is constructed of urethane.

In another embodiment the deformable cup is constructed and arranged to allow for use with a wide range of prosthetic limbs.

In another embodiment the connecting plate further includes a plurality of threaded standoffs.

In another embodiment the coupling system further comprises a finishing plate that is constructed and arranged to operatively connect to the threaded standoffs.

In another embodiment the coupling plate includes a circumferential groove for receiving an o-ring.

In another embodiment the coupling system includes an o-ring coupled to the circumferential groove.

In another embodiment the coupling plate includes a centering hole for operatively connecting to a suspension sleeve assembly.

Another embodiment of the present invention is directed to a coupling system for coupling a prosthetic limb socket to a prosthetic limb structural assembly. The coupling system includes a deformable cup including an amount of magnetic material disposed within the deformable cup and a coupling plate operatively connected to the deformable cup.

In one embodiment the coupling system includes a magnetic disc constructed to attach to a suspension sleeve. In another embodiment the coupling system includes a metallic disc constructed to attach to a suspension sleeve.

Another embodiment of the present invention is directed to a method of making a prosthesis for attachment to an amputated limb. The method includes steps of preparing a positive model of the amputated limb, providing a prosthetic coupling device comprising a deformable cup operatively connected to an attachment plate comprising a bottom surface and a top surface having a plurality of threaded standoffs and a groove for receiving an o-ring, placing the prosthetic coupling device on the positive model, pulling a first sheet of polyvinyl alcohol over the prosthetic coupling device and the positive model, securing a first end of the first sheet of polyvinyl alcohol to the coupling plate with an o-ring, trimming the first sheet of polyvinyl alcohol, securing a second end of the first sheet of polyvinyl alcohol to a vacuum pump, pulling a vacuum with the vacuum pump, pulling at least one layer of dry lamination material over the first sheet of polyvinyl alcohol and interweaving the dry lamination material between the threaded standoffs, attaching a finishing plate to the threaded standoffs with a plurality of set screws, pulling a second sheet of polyvinyl alcohol over the dry lamination material and securing on a first end to a vacuum pump and tying or clamping a second end, introducing a resin material between the first sheet of polyvinyl alcohol and the second sheet of polyvinyl alcohol, pulling a vacuum on the second sheet of polyvinyl alcohol and removing the finishing plate.

In another embodiment of the present invention the method of making a prosthesis for attachment to an amputated limb further includes the step of releasing the vacuum on the first sheet polyvinyl alcohol and repositioning the coupling system prior to pulling the vacuum on the second sheet of polyvinyl alcohol.

BRIEF DESCRIPTION OF THE DRAWINGS

For a better understanding of the present invention, reference is made to the drawings, which are incorporated herein by reference, and in which.

DETAILED DESCRIPTION

For purpose of illustration, and not to limit generally, the present invention will now be described with specific reference to lower extremity prosthetic coupling systems, which are used for attaching an endoskeletal or exoskeletal prosthetic limb structural assembly to a prosthetic limb socket and for connecting a prosthetic limb socket to a suspension sleeve. One skilled in the art will appreciate, however, that embodiments of the present invention are not limited to lower extremity prosthetic devices, but rather, the coupling apparatus and methods in accordance with embodiments of the present invention may be used in other applications requiring coupling of orthotic and prosthetic devices.

Figure 1:
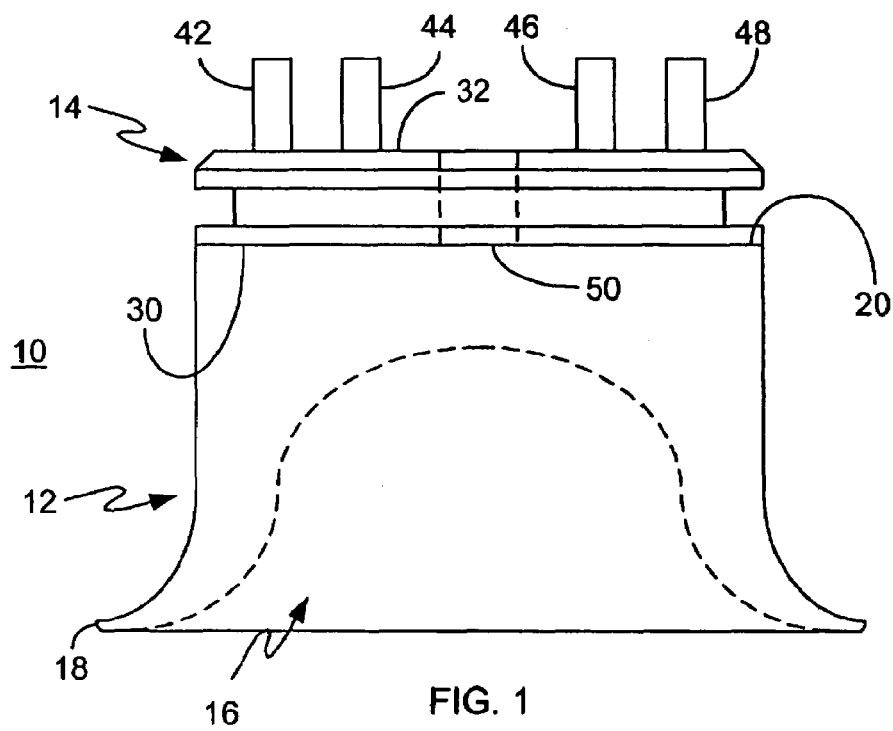
FIG. 1 is a side view of a prosthetic coupling device in accordance with a first embodiment of the present invention.
Figure 2:
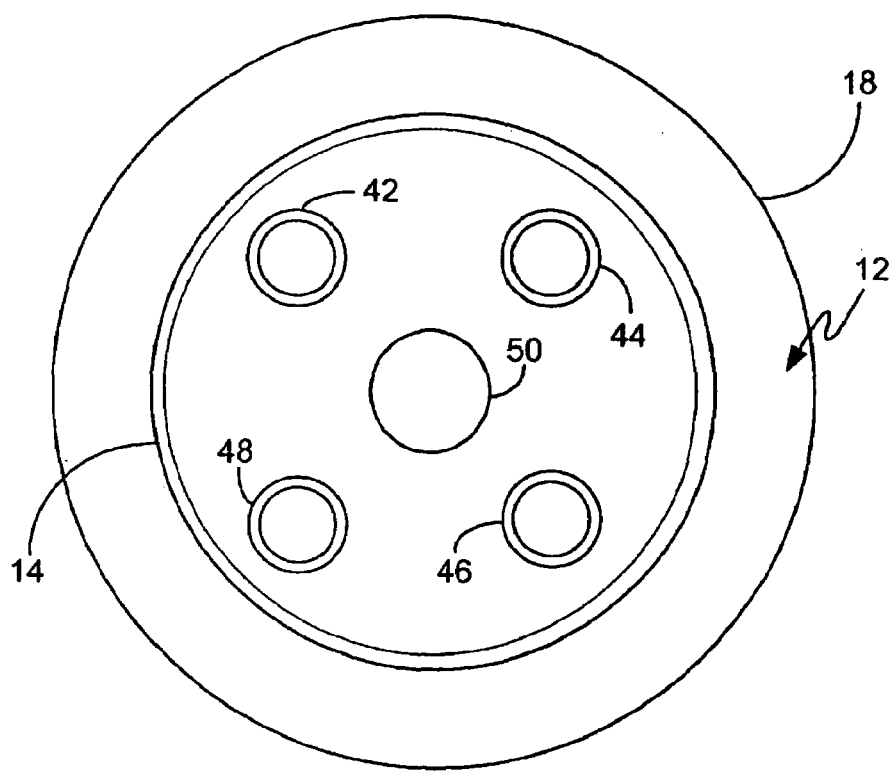
FIG. 2 is a top view of the prosthetic coupling device of FIG. 1.

FIGS. 1–9 show various side and top views of a prosthetic coupling device. Referring now to FIGS. 1 and 2, a prosthetic coupling device 10 in accordance with a first embodiment of the present invention is shown. The prosthetic coupling device 10 comprises a deformable cup 12 operatively connected to a coupling plate 14. Deformable cup 12 includes a lower cupped portion 16 having a flared rim 18 and an upper surface 20. The flared rim 18 is designed to allow the prosthetic coupling device 10 to accommodate a variety of different shaped positive limb models (not shown). Deformable cup 12 is preferably made from a flexible material such as urethane, however, other suitable materials such as rubber and the like may be used.

The coupling plate 14 includes a lower surface 30 for receiving and connecting to the upper surface 20 of deformable cup 12. In the present embodiment, the coupling plate 14 is adhered to the deformable cup with an adhesive layer (not shown); however, other methods are contemplated. The coupling plate 14 further includes an upper surface 32, an o-ring groove 34 located between the lower surface 30 and upper surface 32 and a set of threaded standoffs 42, 44, 46 and 48, which are shown protruding from the upper surface 32. The coupling plate 14 may further include a centered opening 50 passing between the upper surface 32 and the lower surface 30.

Figure 3:
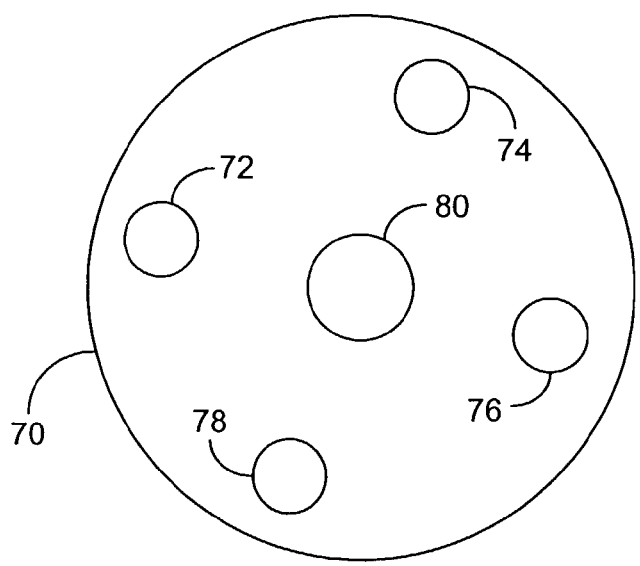
FIG. 3 is a top view of a finishing plate in accordance with a first embodiment of the present invention.
Figure 4:
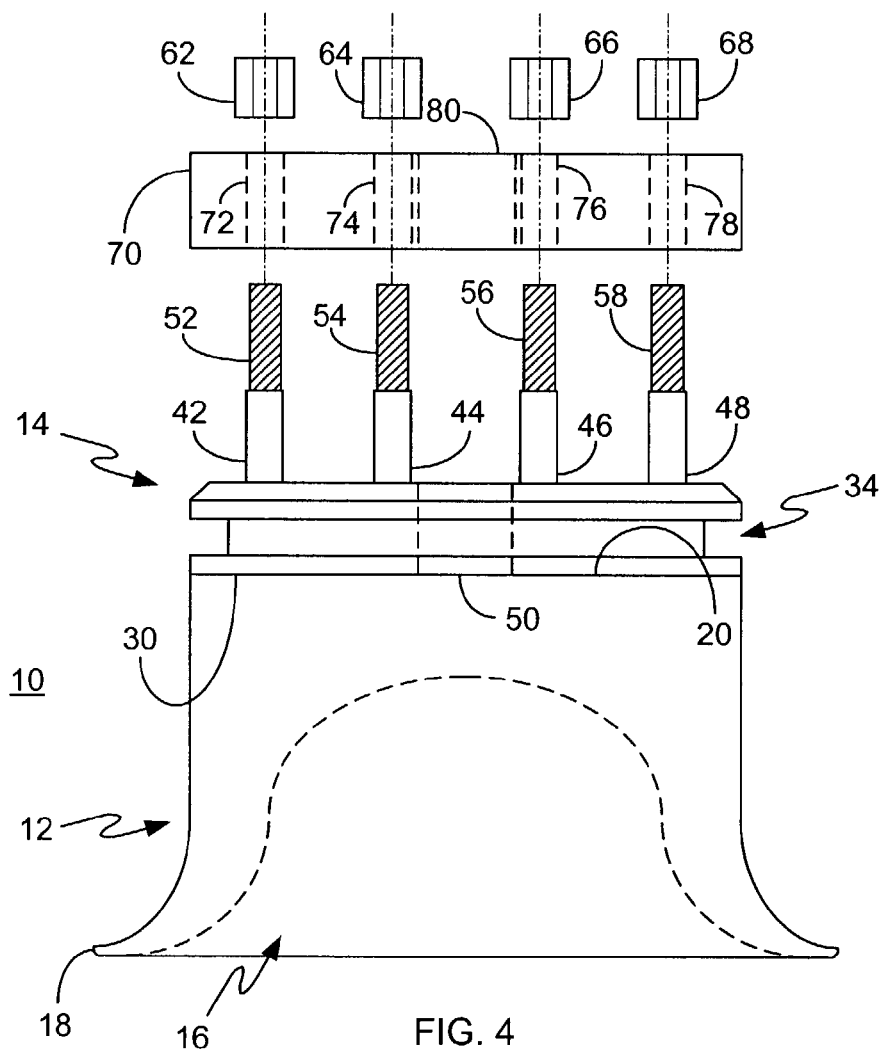
FIG. 4 is a side view of the prosthetic coupling device of FIG. 1 in cooperation with the finishing plate of FIG. 3.
Figure 5:
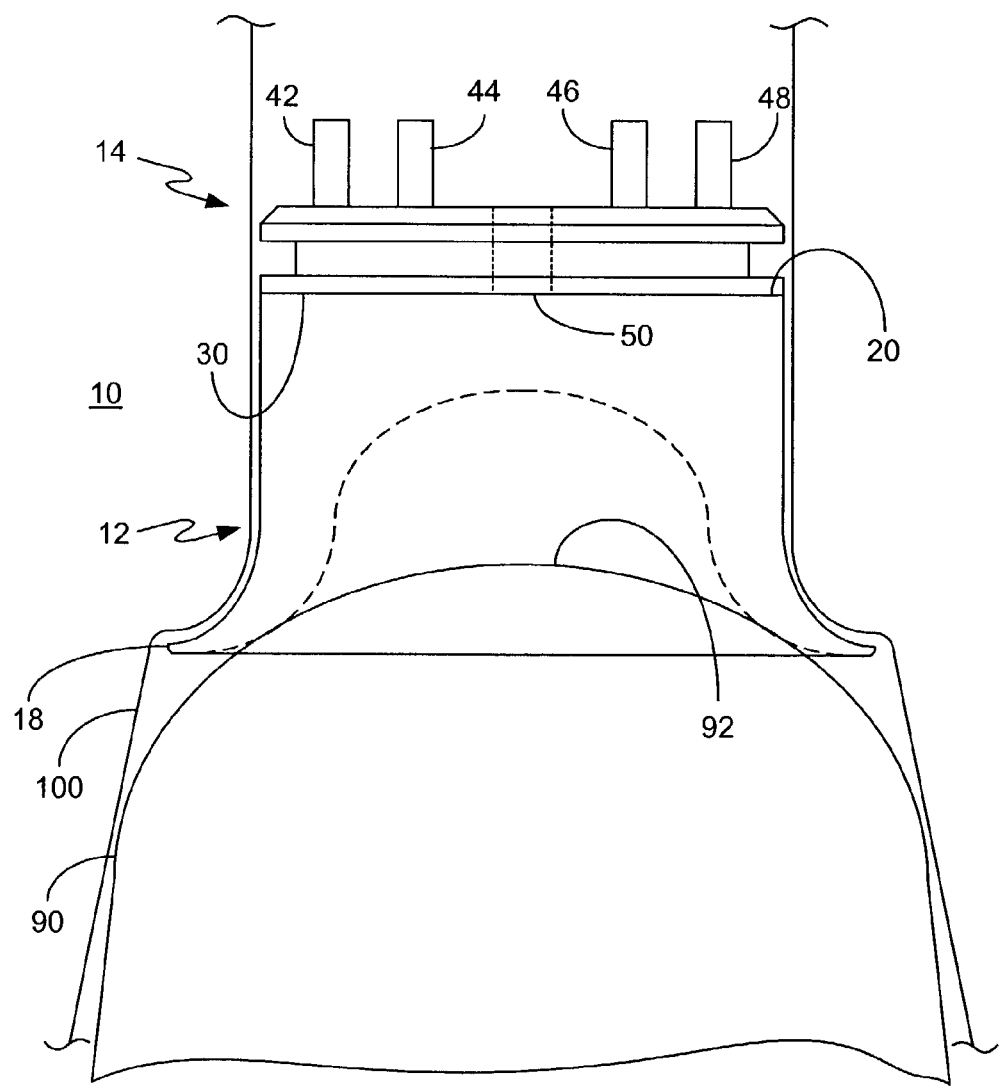
FIG. 5 illustrates the prosthetic coupling device of FIG. 1 cooperating in a first position with a positive model of an amputated limb having received a sheet of PVA material.
Figure 6:
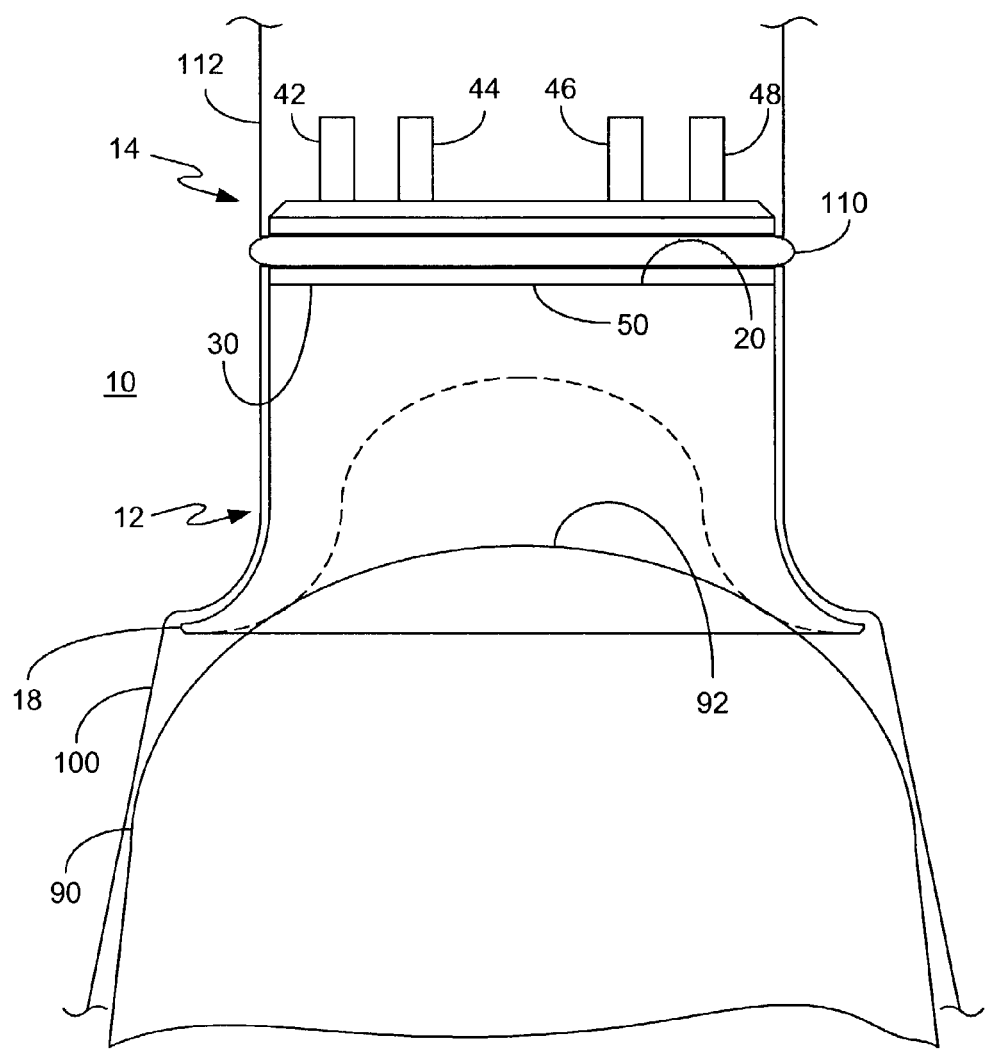
FIG. 6 illustrates the prosthetic coupling device of FIG. 1 receiving an o-ring for securing the PVA sheet of FIG. 5.
Figure 7:
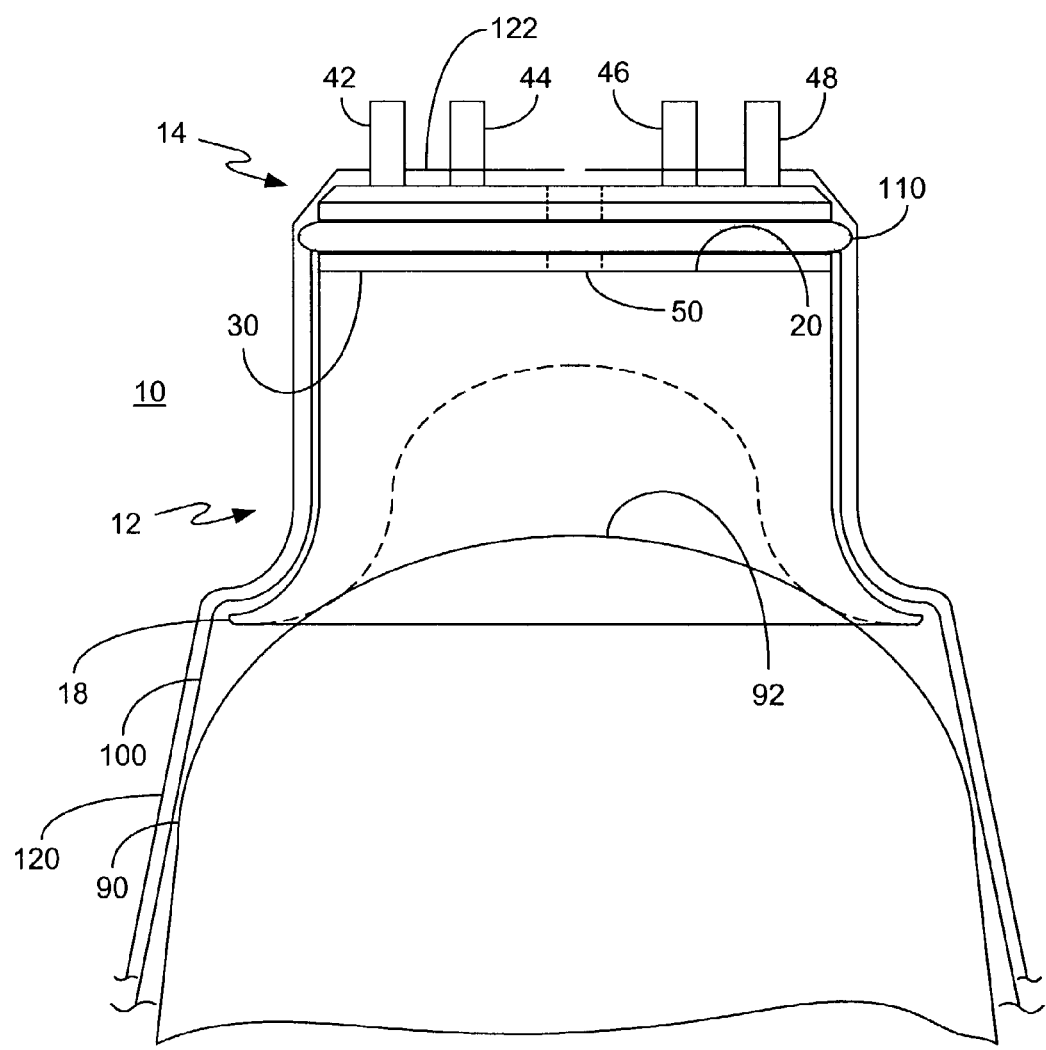
FIG. 7 illustrates a layer of dry material encompassing the prosthetic coupling device, the positive model and the PVA sheet of FIG. 6.
Figure 8:
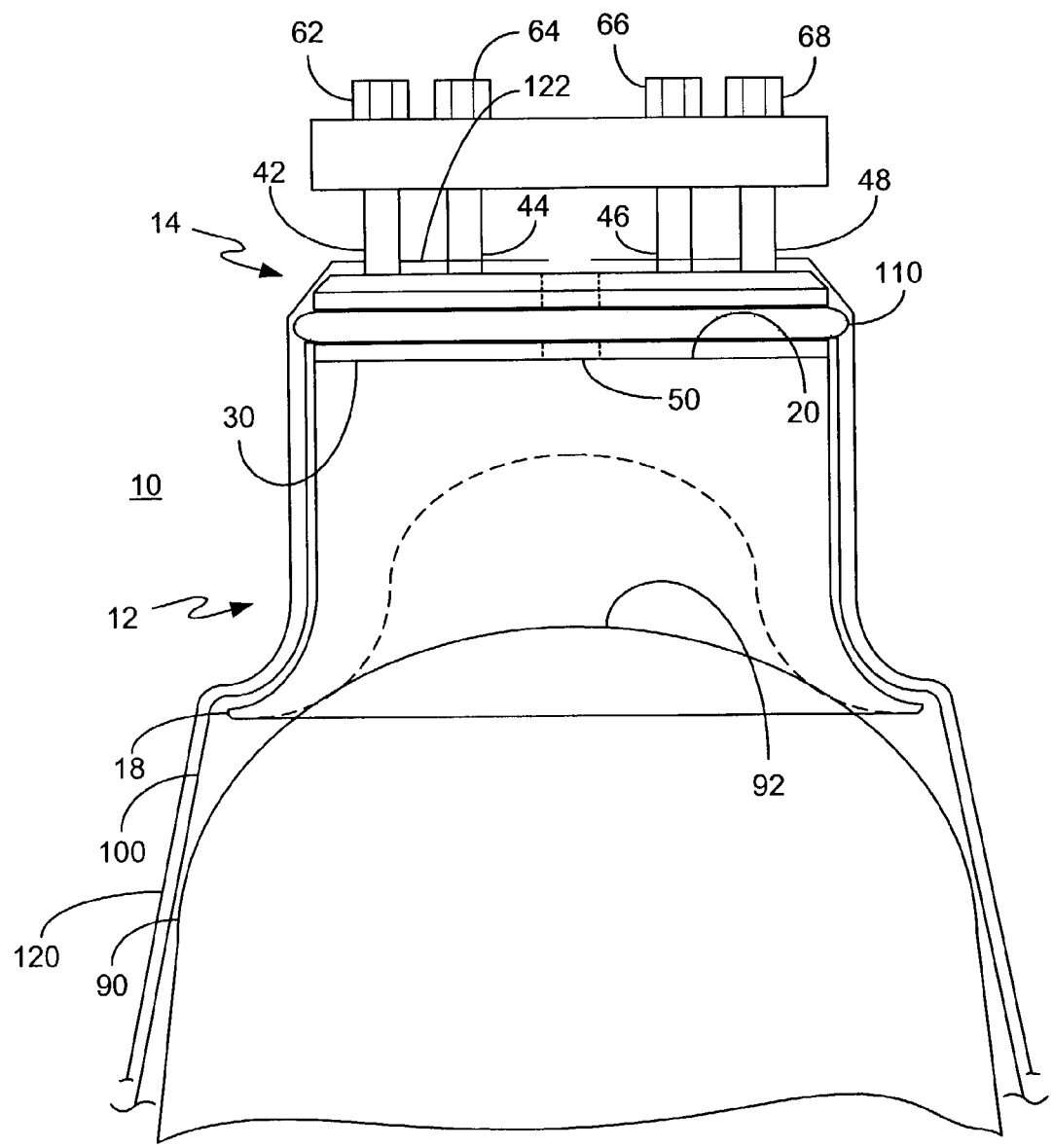
FIG. 8 illustrates the prosthetic coupling device receiving the finishing plate of FIG. 3.
Figure 9:
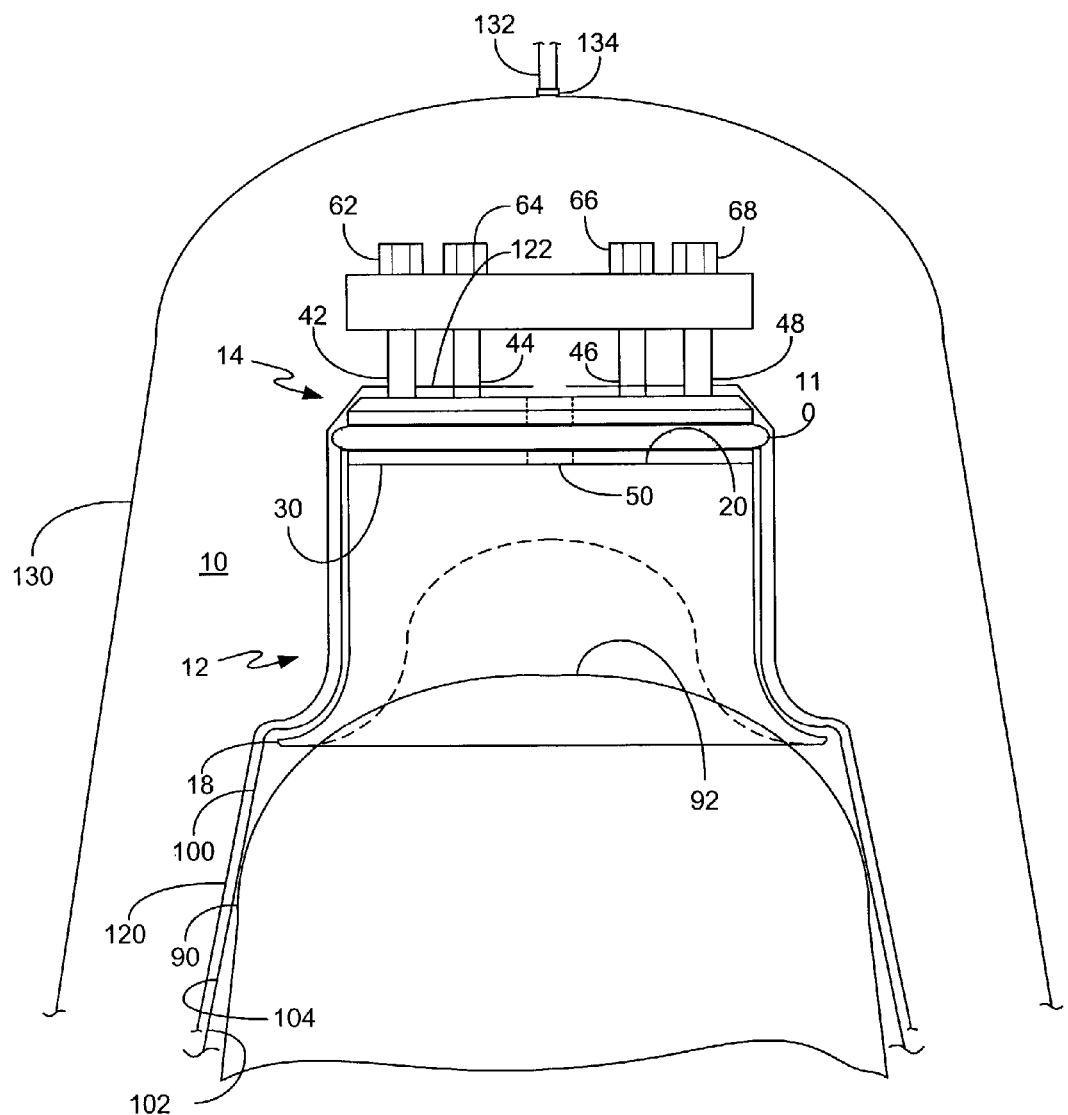
FIG. 9 illustrates the prosthetic coupling device and other components of FIG. 8 receiving a second sheet of PVA material.
Figure 10:
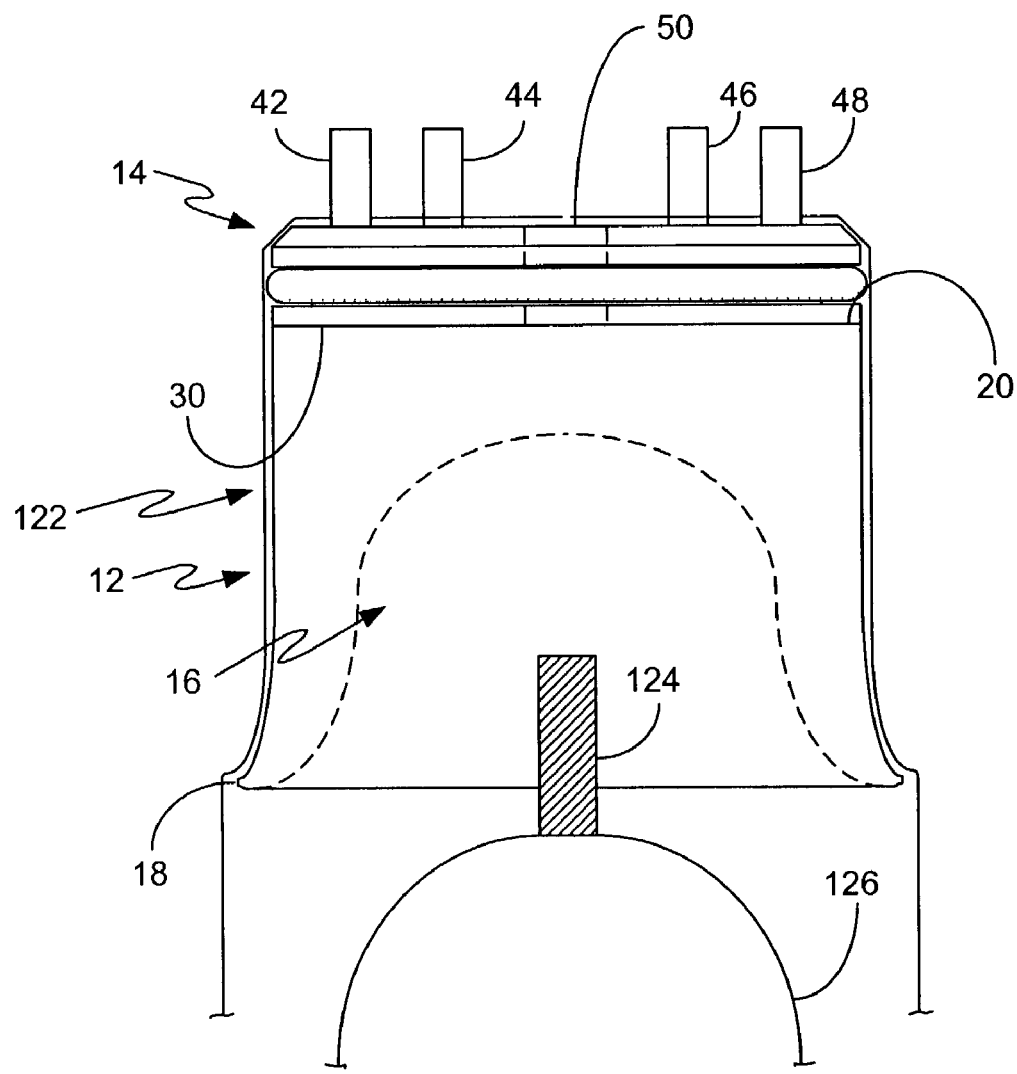
FIG. 10 illustrates a finished prosthetic socket incorporating the prosthetic coupling device of FIG. 1.

Referring now to FIGS. 3 and 4, the prosthetic coupling device 10 further includes an array of setscrews 52, 54, 56 and 58 with corresponding nuts 62, 64, 66 and 68 and a finishing plate 70. The setscrews 52, 54, 56 and 58 are constructed and arranged to threadably engage threaded standoffs 40, 42, 44 and 46. The finishing plate 70 includes an array of through holes 72, 74, 76 and 78 that are arranged to correspond with the placement of threaded standoffs 42, 44, 46 and 48 and a centered through hole 80.

Referring now to FIGS. 5 through 10, the prosthetic coupling device 10 is incorporated into a prosthetic socket. First, a positive model 90 of a residual limb (not shown) is made by one of many known prior art techniques. The positive model 90 acts as a mold for the prosthetic socket. Next, the prosthetic coupling device 10 is set on an end 92 of positive model 90 and a sheet of polyvinyl alcohol (PVA) 100, which has a first side 102 and a second side 104, is pulled over the prosthetic coupling device 10 and positive model 90. The PVA sheet 100, which may be wetted with water to make it more pliable and easier to work with, is secured to the coupling plate 14 with an o-ring 110, thereby forming a bag that completely surrounds the prosthetic coupling device 10 and positive model 90. The o-ring 110 creates an airtight seal and eliminates the need of adding and gluing additional PVA material, a common technique for this prior art prosthetic socket fabrication method. A first end 112 of PVA sheet 100 is then trimmed up to the o-ring 110. A second end of the PVA sheet 100 is secured to a vacuum pump (not shown) and a vacuum is pulled. When the vacuum is pulled, the PVA sheet 100 shapes the deformable cup 12 to the positive model 90. Unlike the prior art apparatus and methods discussed above, if the alignment between the positive model 90 and the prosthetic coupling device 10 needs to be adjusted, the vacuum may be released, the prosthetic coupling device 10 repositioned and the vacuum drawn again.

At least one layer of dry lamination material 120 is then pulled over the PVA sheet 100 and is interwoven over the upper surface 32 of coupling plate 14 such that the dry lamination material 120 is interlaced between the threaded standoffs 42, 44, 46 and 48. Multiple layers of dry lamination material may be used, depending upon the desired thickness of the prosthetic socket. With the dry lamination material 120 in place, the setscrews 52, 54, 56 and 58 are threaded into threaded standoffs 42, 44, 46 and 48. It should be noted that the threaded standoffs could be inserted into the threaded standoffs earlier in the fabrication process. Next, the finishing plate 70 is placed over the setscrews 52, 54, 56 and 58, and is bolted in place with nuts 62, 64, 66 and 68.

With the finishing plate 70 secured in place, a second PVA sheet 130 is pulled over the dry lamination material 120 and secured on one end to the vacuum pump. Next, a liquid laminating resin (not shown) is introduced beneath the second PVA sheet 130. Two types of liquid laminating resin are generally used-polyester and acrylic. It should be noted that other materials may be added to the lamination to increase the strength of the prosthetic socket. These materials include carbon fiber, rayon, Dacron and others.

After the liquid laminating resin is introduced, the PVA sheet 130 is tied off or alternatively clamped at an end 132 with clamp 134 as shown. A vacuum is pulled by the vacuum pump at the other end of PVA sheet 130. The pressure created by the vacuum pump draws the laminating resin into the dry lamination material 120, thereby impregnating the material. In the present invention, the PVA sheet 100 acts as a parting agent and keeps the liquid resin from coming in contact with the positive model 90. After the lamination process is completed the vacuum is released. Next, the nuts 62, 64, 66 and 68, the finishing plate 70 and the setscrews 52, 54, 56 and 58 are removed, revealing a finished prosthetic socket 122 having a uniform laminate layer over the upper surface 32 of the coupling plate 14 that is flush with the openings to threaded standoffs 42, 44, 46 and 48 and that requires little or no adjustment. The length of threaded standoffs 42, 44, 46 and 48 dictate the thickness of the laminate layer over the upper surface 32 of the coupling plate 14.

Also, because urethane has a memory it will want to return to its prevacuumed state. This will cause the deformable cup 12 to spread out tight against the first side 102 of the PVA sheet 100 after the lamination process is completed. The finished prosthetic socket 122 may be attached to a metal pin 124 from a suspension sleeve 126 by any of a number of prior art locking mechanisms (not shown). It should be noted that in addition to the lamination techniques previously described, it is contemplated that the prosthetic coupling device 10 could also be incorporated in a prosthetic socket using thermo-molded plastics, such as polypropylene. Using thermo-plastics would avoid the need to laminate the prosthetic socket and could be done directly over the positive model 90.

Figure 11:
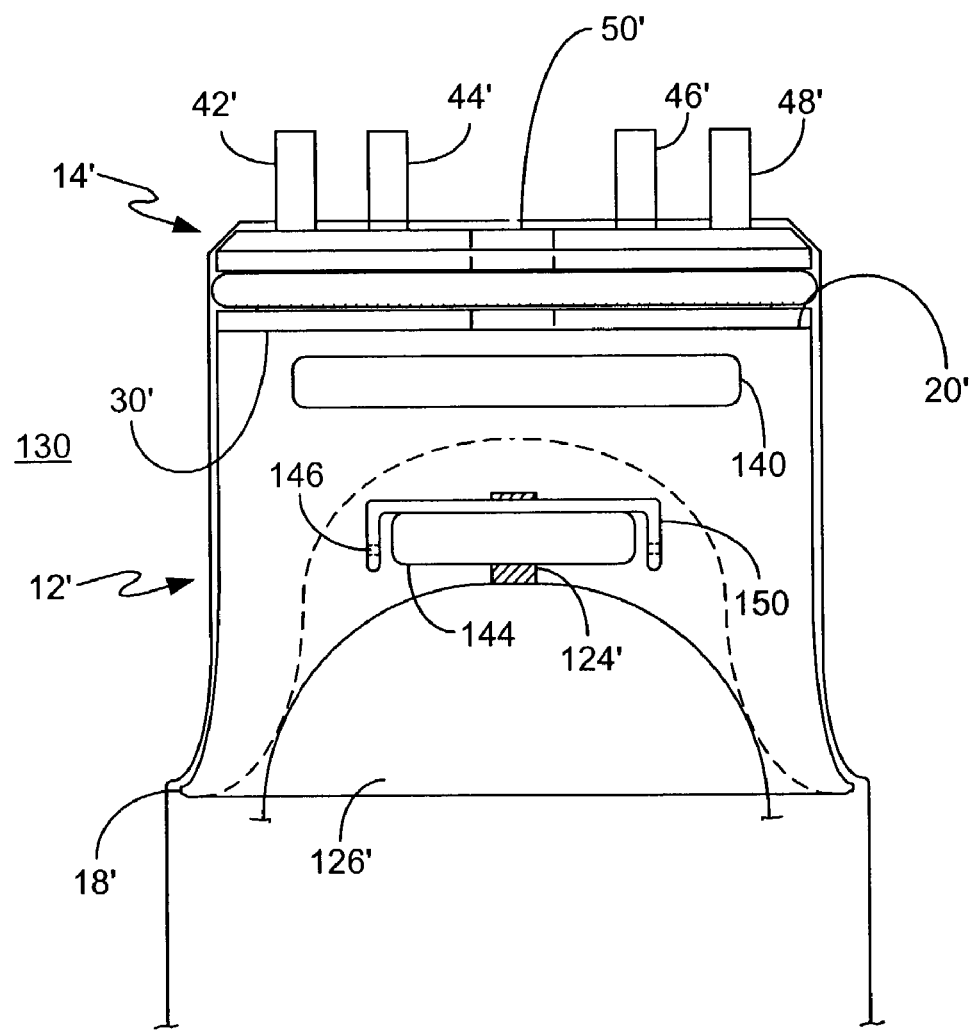
FIG. 11 is a side view of a prosthetic coupling device in accordance with a second embodiment of the present invention.
Figure 12:
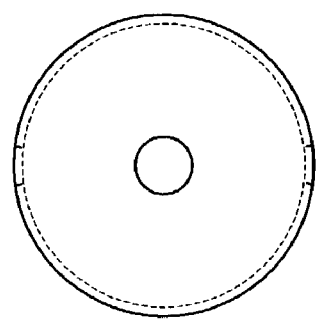
FIG. 12 is a top view of a release mechanism for use with the prosthetic coupling device of FIG. 11.

Referring now to FIGS. 11 through 12, an alternative embodiment of the present invention is disclosed. In this embodiment, an alternative method of attaching a prosthetic socket 130 to a suspension sleeve 126' includes a first magnet 140, which is encapsulated in a deformable cup 12' prior to formation of prosthetic socket 130. The magnet 140 is designed to work in conjunction with a second magnet 144. The second magnet 144 includes a through hole so that it can be easily attached to a metal pin 124' from a suspension sleeve 126'. The magnetic force between the first magnet 140 and the second magnet 144 should be sufficient to secure the prosthetic socket to the suspension sleeve 126' during use. While a two-magnet system is disclosed, other combinations, such as a single magnet and a piece of metal are contemplated. An advantage of this embodiment is that it is both an after-fabrication and an after-market solution and thus may be used in conjunction with prior art locking mechanisms and or prior art suspension sleeves.

In order to release the magnetic bond between the first magnet 140 and the second magnet 144 when removing the prosthetic socket an optional release plate 150 is disclosed. The release plate may include one or more slots 146 to which a release strap (not shown) may be attached. The release strap, when pulled, will allow the wearer to more easily remove the prosthetic device.

Figure 13:
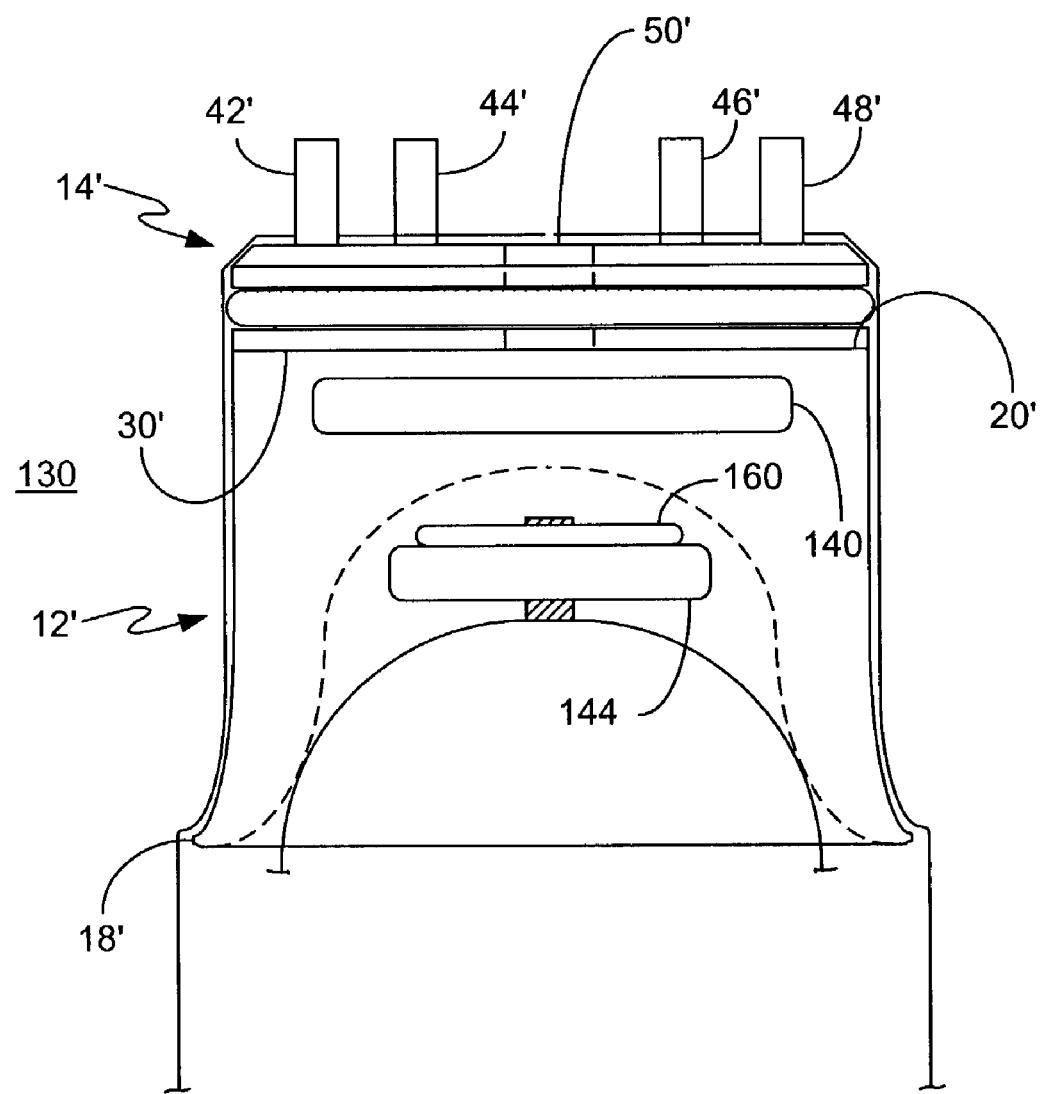
FIG. 13 is side view of a release mechanism in accordance with a third embodiment of the present invention.

Referring now to FIG. 13, an alternative release system for the prosthetic socket 130 is disclosed. In this embodiment, a washer 160 is attached to the end of the metal pin 124' of the suspension sleeve 126'. A hole (not shown) may then be drilled through the side of the prosthetic socket 130 so that a rod or similar device may be inserted between the first magnet 140 and the second magnet 144 to pry them apart. Again, as described above, while a two-magnet system is disclosed in this embodiment, other combinations, such as a single magnet and a piece of metal are contemplated.

Having thus described various embodiments of the present invention, various alterations, modifications and improvements will readily occur to those skilled in the art. Such alterations, modifications and improvements are intended to be within the scope and spirit of the invention. Accordingly, the foregoing description is by way of example only and is not intended as limiting. The invention's limit is defined only in the following claims and the equivalents thereto.

The invention claimed is:

1. A coupling system for use in fabricating a total contact prosthetic limb socket and for coupling the prosthetic limb socket to a prosthetic limb structural assembly, the coupling system comprising:

a resilient deformable cup having an interior cupped surface and an exterior lower surface, wherein the interior cupped surface is adapted for receiving a positive model of a residual limb and for positioning the coupling system relative to the positive model of the residual limb during fabrication of the prosthetic limb socket;

a coupling plate operatively connected to the exterior lower surface of the resilient deformable cup;

a sheet of material operatively covering an assembly of the coupling plate, the resilient deformable cup and the positive model of a residual limb; and means for operatively securing the sheet of material to the coupling plate thereby enabling a temporary vacuum to be created between the positive model of a residual limb and the sheet of material during fabrication of the prosthetic limb socket wherein said vacuum causes the interior cupped surface of the resilient deformable cup to conform to an outer contour of the positive model of a residual limb.

2. The coupling system of claim 1, wherein the coupling plate further comprises a circumferential groove for receiving an o-ring and wherein the means for operatively securing the sheet of material to the coupling plate includes an o-ring removably connected to the coupling plate at the circumferential groove.

3. The coupling system of claim 1, wherein the resilient deformable cup includes a flared rim, which enables the coupling system to accommodate a variety of different shaped positive limb models.

4. The coupling system of claim 1, wherein the coupling plate further includes a plurality of threaded standoffs.

5. The coupling system of claim 4 further comprising a finishing plate, wherein the finishing plate is constructed and arranged to operatively connect to the threaded standoffs.

6. The coupling system of claim 1, wherein the coupling plate includes a centering hole for operatively connecting to a suspension sleeve assembly.

7. The coupling system of claim 1, wherein the resilient deformable cup further includes an amount of magnetic material disposed within the resilient deformable cup.

8. The coupling system of claim 7 further comprising a magnetic disc constructed to attach to a suspension sleeve.

9. The coupling system of claim 7 further comprising a metallic disc constructed to attach to a suspension sleeve.

10. A coupling system for use in fabricating a total contact prosthetic limb socket and for coupling the prosthetic limb socket to a prosthetic limb structural assembly, the coupling system comprising:
   a coupling plate having an upper surface and a lower surface;
   a plurality of internally threaded standoff spacers operatively connected to the lower surface of the coupling plate; and
   a finishing plate, wherein the finishing plate is removably connected to the threaded standoff spacers such that the finishing plate may be connected to the threaded standoff spacers during fabrication of the prosthetic limb socket and disconnected from the threaded standoff spacers upon completion of the fabrication of the prosthetic limb socket, thereby facilitating the formation of a substantially uniform layer of laminate material covering the coupling plate and simple access to the threaded standoff spacers upon completion of the fabrication of the prosthetic limb socket.

11. The coupling system of claim 10, wherein the coupling plate further includes a circumferential groove for receiving an o-ring.

12. The coupling system of claim 11, wherein the coupling system includes an o-ring coupled to the circumferential groove for receiving a sheet of polyvinyl alcohol and wherein the o-ring enables a temporary vacuum to be created between the coupling system, a positive model of a residual limb and the sheet of polyvinyl alcohol during fabrication of the prosthetic limb socket.

13. The coupling system of claim 10, wherein the coupling plate includes a centering hole for operatively connecting to a suspension sleeve assembly.

14. The coupling system of claim 10, further comprising a resilient deformable cup having an interior cupped surface and an exterior lower surface operatively connected to the upper surface of the coupling plate, wherein the interior cupped surface is adapted for receiving a positive model of a residual limb and for positioning the coupling system relative to the positive model of the residual limb during fabrication of the prosthetic limb socket, which allows for the fabrication of a total contact prosthetic limb socket.

* * * * *